United States Patent
Brainard, II

(10) Patent No.: US 6,245,014 B1
(45) Date of Patent: Jun. 12, 2001

(54) FITNESS FOR DUTY TESTING DEVICE AND METHOD

(75) Inventor: Edward C. Brainard, II, Marion, ME (US)

(73) Assignee: Atlantic Limited Partnership, Marion, ME (US)

(*) Notice: Subject to any disclaimer, the term of this patent is extended or adjusted under 35 U.S.C. 154(b) by 0 days.

(21) Appl. No.: 09/442,468

(22) Filed: Nov. 18, 1999

(51) Int. Cl.$^7$ .................................................. A61B 5/00
(52) U.S. Cl. ..................... 600/300; 600/595; 600/587; 128/898; 345/978
(58) Field of Search ..................... 600/300–301, 600/587, 595; 128/897, 898, 903, 905; 345/156, 501, 37, 949, 977, 978

(56) References Cited

U.S. PATENT DOCUMENTS

| | | |
|---|---|---|
| 3,924,852 | 12/1975 | Tamol . |
| 4,142,724 | 3/1979 | Reick . |
| 4,195,643 | 4/1980 | Pratt, Jr. . |
| 4,885,687 | 12/1989 | Carey . |
| 5,388,591 | 2/1995 | De Luca et al. . |
| 5,524,637 | * 6/1996 | Erikson ................................. 600/300 |
| 5,525,061 | 6/1996 | Lord . |
| 5,751,273 | 5/1998 | Cohen . |
| 5,855,373 | 1/1999 | Chen . |
| 6,072,467 | * 6/2000 | Walker ................................. 345/157 |

OTHER PUBLICATIONS

By J. Howard et al., "A Randomized Trial on the Effects of Alcohol on Safety Sensitive Occupational Performance: Simulated Merchant Ship Handling", Jul. 1999, pp. 1–24.

By J. Howland et al., "Employee Attitudes Toward Work–Site Alcohol Testing", *Joem*, vol. 38, No. 18, Oct. 1996, pp. 1041–1046.

By M. Burns et al., "Alcohol's Effect on Cognition", *Alcohol World Health & Research*, vol. 19, No. 2, 1995, pp. 159 and 160.

By J. Collons et al., "The effects of visual input on open–loop and closed–loop postural control mechanisms", *NeuroMuscular Research Center and Dept. of Biomedical Engineering*, 1995, pp. 151–163.

* cited by examiner

Primary Examiner—Eric F. Winakur
Assistant Examiner—Michael Astorino
(74) Attorney, Agent, or Firm—Young & Thompson

(57) ABSTRACT

A fitness for duty (FFD) testing device and method for determining fitness for duty using a testing unit that is held in two hands by a human test subject. Two handles are provided for holding the unit which includes a video screen with an image of a moving shape on a surface. The position of the shape on the screen is determined by the orientation of the hand-held unit. Tilting the unit by the test subject results in the shape moving on the screen. The device computes a score which can be compared to historical results for the test subject, and to results from a larger population base. The FFD device may be programmed to present increasing levels of difficulty as test subject learning occurs, and can receive and provide data to external computing, printing, display, network, or storage devices.

31 Claims, 3 Drawing Sheets

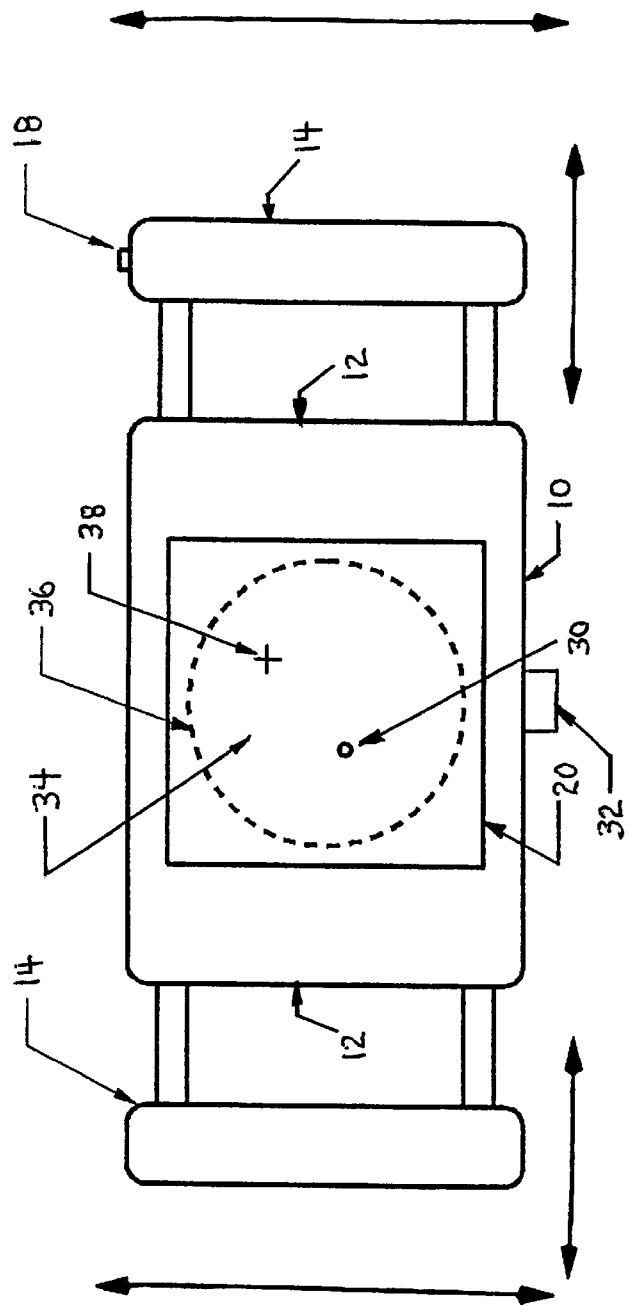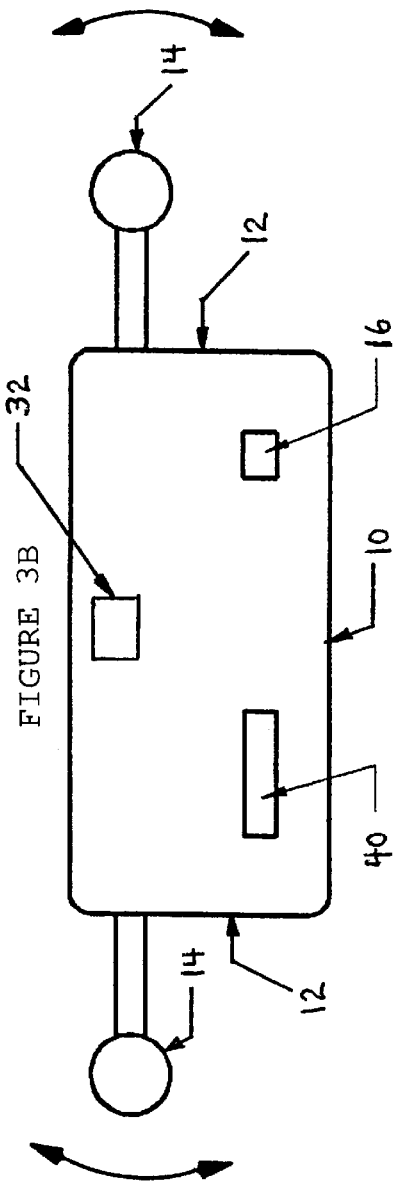

FITNESS FOR DUTY TESTING DEVICE AND METHOD

BACKGROUND OF THE INVENTION

1. Field of the Invention

The present invention relates to devices for measurement of human impairment, which might occur as the result of low-level alcohol or drug exposure or hangovers among other physiological factors, and more particularly to a hand-held fitness for duty (FFD) tester which adapts for human learning during the test and determines a test score which may be used to determine the test subject's fitness for duty.

The definition of FFD tests are well-documented by Burns and Hiller-Sturmhofel ("Alcohol's Effect on Cognition", Alcohol World Health & Research, Vol. 19, No. 2, 1995), but to date, no suitable instrument has been available to accomplish these tasks. The performance criteria for such an instrument include sensitivity to small changes in blood alcohol concentration (BAC), detection of concentrations of BAC below 0.05 percent, reliable and repeatable results, ease and simplicity of test administration, reasonable price, adjustment for learning when a test subject uses the device on a routine basis, establishment of a baseline for each person tested, providing a comparison against a database of similar individuals, updating each individual's baseline to account for learning, and measurement of job or safety-related skills.

Significant work has been carried out by Jonathan Howland, et al. at Boston University School of Public Health which indicates significant performance effects for low-level alcohol exposure (0.04 gm % BAC) for persons performing on diesel engine and ship bridge control simulators ("A Random Trial on the Effects of Alcohol on Safety Sensitive Occupational Performance: Simulated Merchant Ship Handling" (Draft), Jul. 6, 1998). Howland's preliminary findings tend to confirm earlier Boston University survey data from the workplace drinking study ("Employee Attitudes Towards Work-Site Alcohol Testing", JOEM, Vol. 38, No. 10, October 1996) which indicate an association between drinking alcohol at lunch (low-level exposure) and workplace performance impairment or safety problems. Studies using flight simulators, automobile simulators, and industrial task simulation also indicate impairment due to low-level intoxication or hangovers. Furthermore, research appears to indicate that neither the exposed subjects nor their co-workers are aware of this impairment.

From a safety management perspective, these findings pose problems because the effects of low-level alcohol exposure and hangovers are difficult to detect for at least two reasons. First, detection is difficult because affected workers and their co-workers are unable to discern impairment at low-levels of exposure, and secondly, alcohol may have residual impairing effects even when BAC is zero.

Managers in industry, commerce, and government are very much in need of a system that will effectively and efficiently evaluate an employee's fitness for duty without intrusive testing, and regardless of cause (e.g. alcohol, illegal drugs, lack of sleep, or side-effects of prescribed medication). Such an FFD testing system would have application to a broad range of industrial settings involving safety-sensitive work such as aircraft pilots and mechanics, nuclear power plant workers, train engineers, truck drivers, aircraft controllers, ship bridge or engineering personnel, or surgeons.

Finding a rapid and simple FFD device or test would potentially have broad application in these safety-sensitive industries, and could solve the problem of detection and confirmation with employees of any low-level impairment without unduly exposing either the employer or employee to legal liability for the testing procedure or accidents resulting the low-level impairment. Such a system could possibly facilitate self-imposed behavior modifications or seeking of substance abuse counseling by employees who repeatedly fail to pass the FFD test.

The commercial applications of such a FFD test are very large, and present a significant market in response to high, pent-up demand for such a device by the airlines, railroads, trucking companies, and ship operators, among other industries and commercial or governmental organizations.

2. Description of the Related Art

The use of a pressure plate was considered to determine neuromuscular responses. U.S. Pat. No. 4,195,643 discloses a pressure plate for testing lameness of horses suffering from arthritis, septic tendinitis, and hair-line fractures. The device uses time and frequency-domain analysis to determine physiological conditions of the animal under test. A block diagram of this approach is shown in FIG. 1.

U.S. Pat. No. 5,388,591 expands the application of the pressure plate to the analysis of the human postural control system by employing statistical analysis of the random displacement of the center of pressure of the subject while standing on the pressure plate, as depicted in FIG. 2.

Although use of a pressure plate may initially appear useful for FFD testing, there are drawbacks to its use. From a safety perspective, requiring a subject to stand on a platform 40 cm by 40 cm which is several centimeters high may create a potentially unsafe condition, particularly if the individual under test has poor balance due to drug or alcohol impairment, poor health, or other physiological factors. This problem may be exacerbated if the subject is asked to balance on one foot to perform a test having the greatest sensitivity to balance. In addition, the pressure plate does not have a means to "push" the subject to higher levels of work effort; the pressure plate test is simply a measure of balance.

OBJECTS AND SUMMARY OF THE INVENTION

With these limitations of the prior art in mind, it is an object of the present invention to provide a novel, non-intrusive, practical, and relatively inexpensive FFD testing device and method.

It is also an objective of the present invention to provide a testing device which requires conscious effort beyond balance alone, which uses visual inputs and requires two hands for execution, and a test method which uses this device that is easy to administer.

It is further an object of the present invention to provide a testing device and method which uses neuromuscular, vestibular, visual, and cognitive skills, like the demands of tasks in the workplace, and which provides repeatable and easily measurable results.

It is still further an objective of the present invention to allow the test subject to work in its most advantageous mode to carry out the test and to eliminate any concern over left or right-handedness of the test subject.

It is yet further an object of the present invention to adapt to human learning during conduct of the test and to increase difficulty of the test in response to the learning by the test subject.

It is another objective of the present invention to store and compare test results of the individual test subject and of a larger population base of test subjects.

It is further another object of the present invention to be able to uniquely identify each test subject.

It is still further another objective of the present invention to be able to program initial test conditions and dynamic characteristics of the test.

It is yet further another object of the present invention to provide output to external devices or databases, and to receive input from external devices or databases.

It is an additional objective of the present invention to utilize existing, commercially available processing electronics, and to use software algorithms based on basic physical principals.

In accordance with the claimed invention, a FFD testing device and method is thus provided which can meet the foregoing objectives.

The FFD test device and method are used to determine the fitness for duty of employees in industry, commerce, government, research, and medical professions. The device includes a hand-held unit which is used in an upright, standing position and is held by the person being tested with both hands in front of their body. The hand-held unit contains electronic sensors for determining the orientation of the hand-held unit in space or in the earth's gravitational field. Upon initializing the device, an image of a ball or other shape, a "virtual" image, appears on a screen in the hand-held unit. The goal of the test is to maintain the position of the ball at a target position, such as in the center of the screen, by tilting the hand-held unit. The ball appears to "roll" on a "virtual" surface in simulated response to gravity, depending on the unit's orientation. Any tilting of the device from this plane by the human test subject results in the ball moving from the target position as if gravity were acting on the ball.

The FFD testing device computes a test score based on the test subject's ability to maintain the ball in close proximity to the target position, and the device establishes a baseline of historical test results of the test subject and test results of a larger population, both of which may be compared to the test subject's score. In addition, the FFD testing device can dynamically adapt the difficulty of the test as the test is being conducted in order to account for learning and increased familiarization with the device by the test subject. Such "pushing" of the test subject to higher levels of work effort is accomplished by introduction of sudden transients of ball position, or virtual surface characteristics which would act to stress the test subject beyond the typical 32 millisecond (31.25 Hz) neural response of the human muscular system.

These and other objects and advantages of the present invention will be apparent to those with skill in the art from a reading of the detailed description of the preferred embodiments, which is given with reference to the accompanying drawings.

BRIEF DESCRIPTION OF THE DRAWINGS

FIGS. 3A and 3B are top and side exterior views of an embodiment of the present invention.

DETAILED DESCRIPTION OF THE PREFERRED EMBODIMENTS

Figure 1:
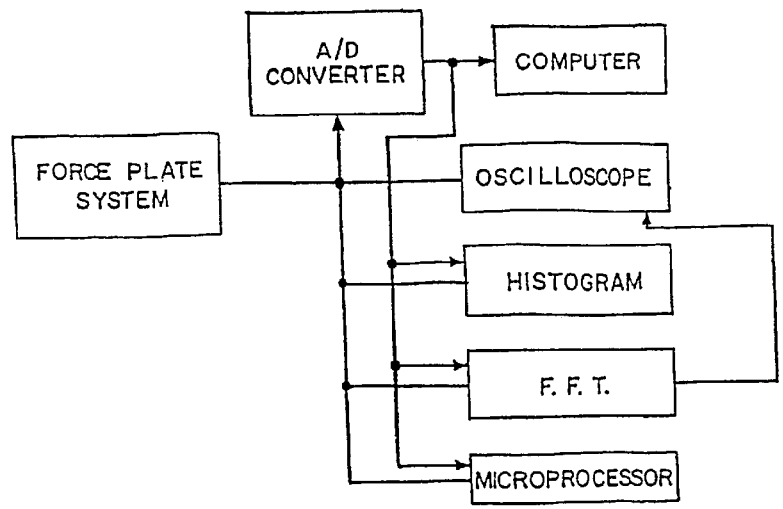
FIG. 1 shows a prior art device in block diagram form for measuring and analyzing input forces using a force plate system as the transducer.
Figure 2:
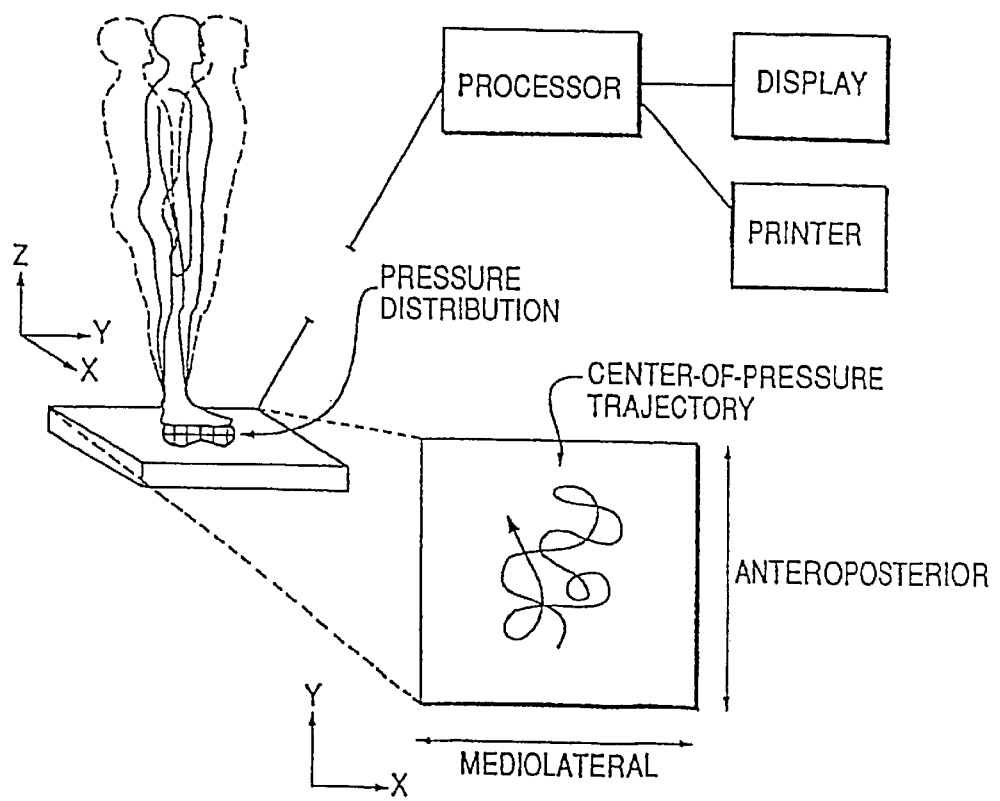
FIG. 2 shows a prior art apparatus in block diagram form for analyzing the human postural control system.

With reference to FIGS. 3A–3B, a first embodiment of a hand-held FFD testing device for determining the fitness for duty of a human test subject may include a hand-held enclosure 10 having a top and at least one exterior side surface 12 to which are attached at least two handles 14 on generally opposite radial sides of the enclosure 10 and that are each to be held by a different hand of the human test subject. However, these handles may be adjustable in a variety of ways, i.e. either into or away from, fore and aft, or up and down relative to the enclosure to accommodate an individual test subject's grip, as depicted by the arrows in FIGS. 3A and 3B. A main power switch 16 may be provided to activate the device by providing power to internal electronic processing and display components discussed below, and a push-button test initiation switch 18 may also be provided for use by the human test subject to initiate the FFD test. The top of the enclosure 10 includes a display screen 20 discussed below.

The enclosure 10 houses an accelerometer 22 (FIG. 4) having at least two independent outputs 24 representing acceleration components along at least two perpendicular axes, and preferably having three independent outputs representing acceleration components along three orthogonal axes. The outputs 24 are provided to an analog-to-digital converter (ADC) 26. Outputs 24 include data indicative of the orientation of the enclosure 10 relative to a frame of reference, such as the earth's gravitational field.

The accelerometer 22 may be of any commercially available type, such as potentiometric, reluctive, strain-gage, servo, piezoelectric, mechanical gyro, fiber-optic gyro, and ring-laser gyro type, however it preferably is a Crossbow Technology, Inc. Model CXL02LF3 Triaxial Accelerometer, having a range of +/−2 g in each axis with an analog output of 0 to +4 volts for each axis, and a bandwidth of 0–125 Hz. in all three axes. The digital outputs from ADC 26 provide data which represent the acceleration seen by the accelerometer 22 that are preferably digitized to a 12-bit resolution at 250 Hz., and provided as inputs to a processor 28, which is preferably a digital microprocessor housed in the enclosure 10, or in an external system.

Processor 28 receives and analyzes the accelerometer data and provides fitness for duty test results based on this information by using software algorithms implementing well-known integration techniques to derive positional information from the acceleration data. By using standard equations of motion for velocity and displacement using calculated acceleration, i.e. $v=v_0+at$, and $x=x_0+v_0t+\frac{1}{2}at^2$, the processor determines the position of an image of a moveable shape 30, preferably a standard geometric figure such as a ball, on the screen 20.

The screen 20 is preferably a liquid crystal display (LCD), however, it may be a thin-film electroluminescent display, a cathode ray tube, or a plasma or gas panel type display mounted on the handheld unit or an external unit.

Preferably, the shape 30 is on a surface 34 which can be varied, e.g. rough or smooth, or of differing contours, e.g. flat, conic section, undulating, or spherical, so as to allow the shape 30 to have different movement responses. Movement of shape 30 may be subjected to viscous damping or programmed with non-linear characteristics, and a simulated gravitational constant may be changed. Processor 28 simulates movement of the shape 30 in a plane parallel to the surface 34, and may simulate movement of shape 30 in a direction perpendicular to the surface 34 so as to provide a three-dimensional visual effect on a two-dimensional display 20.

The surface 34 may be bounded by a peripheral boundary wall 36 that may have various interior contours including arcuate and linear. The shape may "bounce" off the wall 36, or off of the exterior edges of screen 20. In the latter event, the wall 36 may merely be a measuring line for evaluating performance. The peripheral boundary wall 36 preferably is equidistant from the center of screen 20, however the placement of the boundary wall 36 may be varied by the test administrator.

These factors are accounted for by the processor software in calculating the vector components of acceleration due to gravity "virtually" acting on the shape 30 as the enclosure 10 is moved by the test subject. These acceleration components are then used in the equations of motion to determine velocity and displacement of the shape 30 on the surface 34. The calculated acceleration components are dependent on the acceleration due to gravity, the tilt of the enclosure 10, the position of the shape 30 on the surface 34, and the type of surface 34 used for the test.

The processor 28 may also determine a test score which may be displayed on the screen 20. The test score may be determined by statistical evaluation of the movement of shape 30 about a target position 38 on the surface 34, or movement of the shape along a defined path shown on the screen 20. Other measures of movement of shape 30 may be used, including average straight path length, maximum extent of movement, percent within a defined limit, time without movement, and the like. Preferably, the target position 38 is the center of the screen 20. For example, the statistics used in the evaluation may include the mean distance of the shape 30 from the target position 38 or from the defined path, as well as other parameters such as the standard deviation, kurtosis, and skew of these measures of movement of the shape 30. These additional statistical parameters provide a fine, detailed analysis of the FFD test subject's performance.

The indicators for target position 38 and the shape 30 may be similar or dissimilar figures that visually facilitate placement of the shape 30 relative to the target position 38. Shape 30 may include a directional arrow indicative of the direction of movement of shape 30 that may be determined by processor 28. A more sophisticated FFD test may include two shapes 30 on surface 34.

The processor 28 preferably employs frequency-domain techniques, such as Fast Fourier Transform (FFT) techniques for further evaluation of the test subject's response, although other suitable algorithms may be used to compute frequency domain characteristics. This evaluation preferably would include spectral and cross-spectral analysis of the data from the accelerometer 20, or positional data derived from the accelerometer data.

Figure 4:
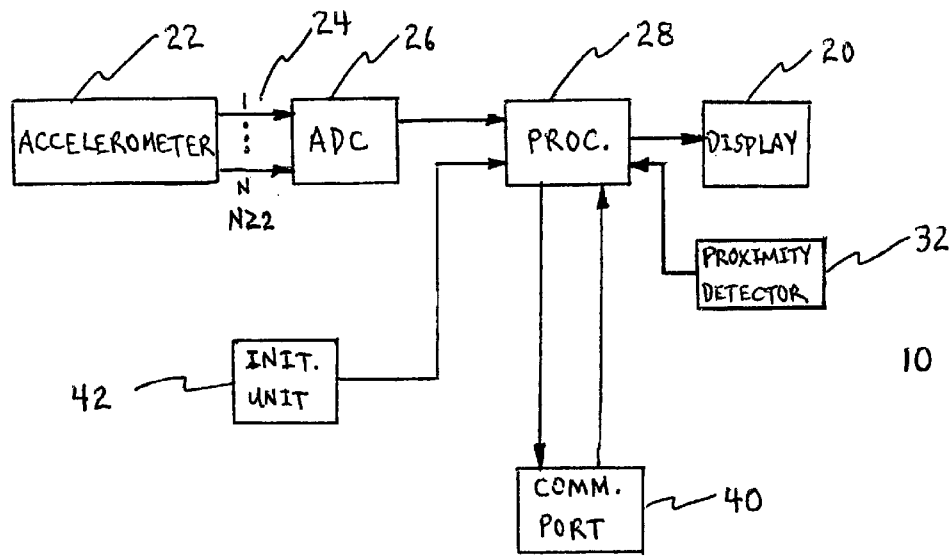
FIG. 4 shows a block diagram of the first embodiment of the present invention.

With reference to FIG. 4, the invention may also include a communication port 40 that allows an output from the processor 28 to be provided to external devices or a computer network, or to provide data to the processor 28 from any suitable peripheral device. The communication port may be of RS-232 serial, parallel, infra-red (IR), radio frequency (RF), universal series bus (USB), or small computer systems interface (SCSI) type, but preferably the communication port is of RS-232 serial type.

The invention may also include an initialization unit 42 connected to the processor 28 to establish desired initial test conditions and desired dynamic test parameters for the device, and to uniquely identify the human test subject.

The desired initial test conditions could include test duration, elasticity of the shape 30, size and shape of the shape 30, shape of the surface 34, shape of the peripheral boundary wall 36, dynamic reflection characteristics of the peripheral boundary wall 36, and simulated friction effects between the shape 30 and the surface 34. To change the difficulty of the FFD test, dynamic test parameters could be pre-programmed to include random transient changes in position of the shape 30, periodic changes in position of the shape 30, changes to the shape and size of the wall 36, changes to the value used for the simulated gravitational constant, and changes to the surface 34.

The initialization unit 42 may comprise a magnetic identification card swipe device, or a keyboard for entry of test subject identification data and a password, or a fingerprint identification device for additional security. The initialization unit 42 may be integral with the enclosure 10, or separate therefrom and communicating with the processor 28 through the communication port 40.

Preferably, the accelerometer 20, the ADC 26, the processor 28, the power switch 16, the push-button test initiation switch 18, and the communications port 40 are all located within the hand-held enclosure 10.

Figure 5:
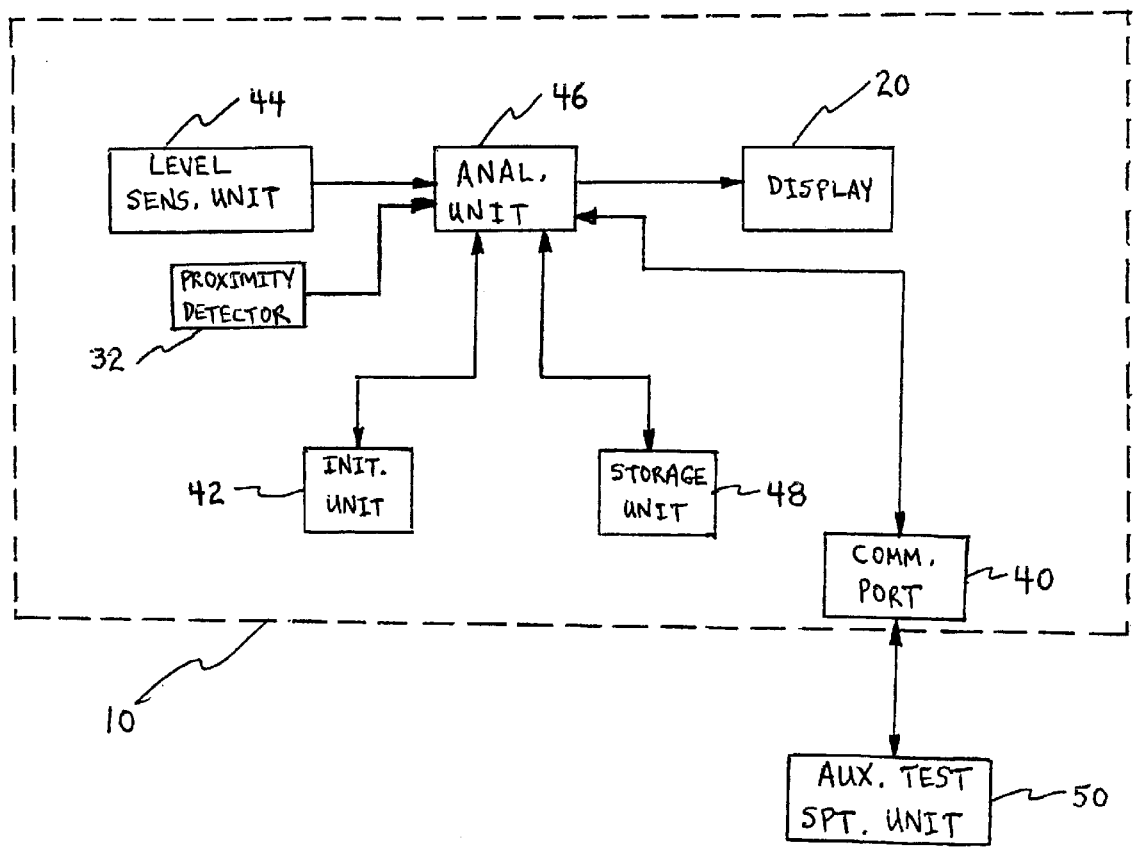
FIG. 5 shows a block diagram of a further embodiment of the present invention.

In an alternative embodiment shown in FIG. 5, the accelerometer 22 may be replaced with a level sensing unit 44 within enclosure 10 for determining the level of enclosure 10 with respect to a plane tangent to the earth's surface. The level sensing unit 44 may be a mechanical gyroscope, fiber-optic gyroscope, ring-laser gyroscope, liquid potentiometer, or preferably, an electric output, two-axis spirit-level type device.

Output from the level sensing unit 44 is provided to an analysis unit 46, also within the enclosure 10, which receives and analyzes the level-sensing data and provides fitness for duty test results based on analysis of this information as in the first embodiment.

The initialization unit 42, in concert with the analysis unit 46, may further adjust the test difficulty in response to learning by the human test subject as the test progresses. The test difficulty is partially determined by the desired initial test conditions and the desired dynamic test parameters which are established by the test administrator or test subject. Learning by the test subject may be indicated by an improving trend of test results. Ideally, for the device to provide meaningful results, one test subject should have relatively consistent results, assuming the test subject is fit for duty each time the test is taken. Of course, some learning is to be expected and thus, in response to an improving trend, the analysis unit 46 may take steps to make the test more difficult, such as speeding up the shape movement, changing surface contours, etc. in order to compensate for learning so that the computed test score may be adjusted to be a relatively consistent number before and after learning has taken place.

A storage unit 48, located within the enclosure 10 and preferably a semiconductor memory type, may be connected to the analysis unit 46 to provide historical test data and level-sensing data storage. Preferably, the storage unit 48 stores current test results and historically achieved results for future comparison of test results for the particular individual under test, or for test comparison among a wider population of test subjects.

The communication port 40 may be connected to an auxiliary test support unit 50, such as a general purpose computer, printer, plotter, or memory storage device, a network, or the internet for further manipulation and presentation of test results.

In addition, to minimize "cheating", a proximity detector 32 (FIGS. 3A, 3B, and 5) may be located on the surface of the device enclosure to ensure the test device does not contact the test subject's body, except at the handles. The proximity detector indicates when the test subject attempts to stabilize the device by resting it on the torso, legs, etc. The proximity detector may be a sonic, capacitive, RF or other appropriate type of detector which provides a signal to the processor 28 in the first embodiment, or to the analysis unit 46 in the second embodiment. The proximity detector may trigger an aural or visual alarm, and the test may be restarted or stopped when "cheating" is detected.

Experimental Results

The FFD device, in prototype form, has been used at the Maine Marine Academy in conjunction with tests using an automated ship's bridge simulator. The objectives of the bridge simulator tests are to determine the effects of alcohol dosing of subjects to determine a safe maximum limit of alcohol concentration in the blood stream. The tests were conducted in March, 1999 under protocols established by the National Institute of Health.

Half of the subjects (five individuals) were dosed to an alcohol blood concentration of 0.04% by body weight ("alcohol group"). The other five subjects ("placebo group") were told they were dosed, but did not receive alcohol.

The test series lasted two evenings. During the first evening, all the subjects received instructions concerning the FFD operation and testing. All subjects had previously received instruction on the bridge simulator and were proficient in its use. Each subject carried out three, one minute tests with the FFD instrument. Test subject scores were determined for the average distance from the center target.

The subjects were each given a drink with an additive to mask the presence of alcohol, however, there was no alcohol in this first drink. After one half hour, the test subjects were given a bridge simulator test which lasted approximately one half hour. At the end of this test, each subject again carried out another set of three, one minute tests with the FFD device.

During the next evening, the same protocol was used, except the drink was dosed with alcohol for the alcohol group. All test subjects carried out FFD tests before and after the bridge simulator test.

Since there can be considerable learning during the first use of the FFD device, the first night's scores were not used for this analysis. During the second night, the average score for the test before the simulator test was subtracted from the average score for each subject after the bridge simulator test.

The average distances of placebo and alcohol-dosed subjects were averaged together for the placebo and dosed groups. A T-test was used to compare the average distances for pre and post-test scores. The means were found to be statistically significant. The placebo mean difference was −0.536, and the dosed alcohol mean change was +0.518, P=0.045. The following table summarizes the experimental results.

| Group | Pre-simulator | Post-simulator | Difference |
| --- | --- | --- | --- |
| Alcohol | 5.9 | 6.5 | +0.518 |
| Placebo | 2.6 | 2.1 | −0.536 |

T-test comparing pre and post-test score changes for 3-trial means scores by experimental group: $P = 0.045$
Regression Model: Post-test 3-trial mean scores = pre-test 3-trial mean scores + alcohol status.
$P = 0.069$ for alcohol status
$P = 0.003$ for pretest score
$R^2$ for model = 0.95
Correlation between post-test mean scores and simulator performance score: $R = 0.74$ Alternative applications of this device are also available outside the fitness for duty testing area. For example, with software modifications, the present invention could be used for entertainment purposes as a video game for one or more persons to play individually or as a team, either by standing, or being seated with the device being hand-held, or mounted to the floor or a table in a resilient fashion, with an objective of the game being to maintain the shape at a predetermined position, or to deny opposing players the ability to maintain the shape at the desired position. Additional handles could be provided for team games in which each team has its own shape 30 of unique color or shape.

While the present invention has been described in connection with certain preferred embodiments, it is to be understood that the invention is defined by the following claims, when read in light of this description and the accompanying drawings, and equivalents thereof.

What is claimed is:

1. A testing device for testing fitness for duty of a human test subject, the device comprising:
   a hand-held, freely-moveable enclosure having a top, at least one exterior side surface, and at least two handles attached to said at least one exterior side surface of said enclosure,
   an accelerometer in said enclosure and having at least two outputs, said at least two outputs each being representative of acceleration along a different one of at least two orthogonal axes, and said at least two outputs providing data indicative of an orientation of said enclosure;
   a processor within said enclosure receiving and analyzing said data and providing fitness for duty test results based on said data; and
   a visual display on said top of said enclosure connected to said processor and providing a visual indication to a human test subject of the orientation of said enclosure.

2. The device of claim 1, wherein said accelerometer has three of said orthogonal axes and three of said outputs, each of said three outputs being representative of acceleration along a different one of said three orthogonal axes.

3. The device of claim 1, wherein said accelerometer is one of potentiometric, reluctive, strain-gage, servo, piezoelectric, mechanical gyro, fiber-optic gyro, and ring-laser gyro type.

4. The device of claim 1, wherein said at least two handles are movably attached.

5. The device of claim 1, wherein said visual display comprises a screen on said top of said enclosure, said screen displaying an image of a shape on a surface bounded by a peripheral boundary wall, a position of said shape on said screen being determined by the orientation of said enclosure.

6. The device of claim 5, wherein said screen is one of liquid crystal, thin-film electroluminescent, cathode ray tube, plasma, and gas panel type.

7. The device of claim 5, wherein said processor comprises a microprocessor receiving said data from said at least two outputs and computing an average distance over time of said shape from a target position on said screen.

8. The device of claim 7, wherein said shape is a ball.

9. The device of claim 7, wherein said microprocessor further conducts frequency-domain analysis of said at least two outputs.

10. The device of claim 9, wherein said frequency-domain analysis of said at least two outputs comprises a Fast Fourier Transform (FFT).

11. The device of claim 5, further comprising an initialization unit establishing initial test conditions and dynamic test parameters for the device, said initial test conditions being at least one of test duration, elasticity of said shape, size of said shape, shape of said surface, shape of said peripheral boundary wall, reflection characteristics of said peripheral boundary wall, and friction between said shape and said surface, and said dynamic test parameters being one of random transient changes in position of said shape, a change in a simulated gravitational constant, and periodic changes in position of said shape.

12. The device of claim 1, further comprising an initialization unit uniquely identifying the human test subject.

13. The device of claim 12, wherein said initialization unit further comprises at least one of a magnetic identification card swipe device, and a keyboard for entry of at least one of human test subject identification data and a password.

14. The device of claim 11, wherein said processor is arranged and constructed to modify dynamic test parameters to account for learning by the human test subject.

15. A system for testing fitness for duty of a human test subject, the system comprising:
    a hand-held enclosure having an exterior surface and two handles attached to said exterior surface, said enclosure being freely moveable by a human test subject;
    a level-sensing unit enclosed within said enclosure and having at least two perpendicular axes for measuring an orientation of the enclosure and providing level-sensing information representative of said orientation;
    a visual display on top of said enclosure having a screen displaying a shape that is moveable on a surface, wherein a position of said shape on said surface is determined by said orientation of said enclosure and said orientation is determined by the human test subject, and wherein said visual display provides visual feedback to aid the human test subject in attempting to maintain said shape at a target position;
    an analysis unit enclosed within said enclosure for analyzing said level-sensing information from said level-sensing unit, determining the position of said shape on said surface in response to said orientation, measuring movement of said shape relative to said target position, and computing a fitness for duty test score based on said movement measurement;
    a storage unit enclosed within said enclosure and connected to said analysis unit for storing said level-sensing information; and
    a communication port on said exterior surface of said enclosure being connected to said processor for at least one of receiving an input and providing an output.

16. The system of claim 15, wherein said level-sensing unit is one of mechanical gyroscope, fiber-optic gyroscope, ring-laser gyroscope, liquid potentiometer, and electric output spirit-level type.

17. The system of claim 15, wherein said communication port is one of RS-232 serial, parallel, infra-red (IR), radio frequency (RF), universal series bus (USB), and small computer systems interface (SCSI) type.

18. The system of claim 15, wherein said level-sensing unit has three perpendicular axes for determining said orientation.

19. The system of claim 15, wherein said two handles are movably attached.

20. The system of claim 15, further comprising an initialization unit connected to said analysis unit for uniquely identifying a human test subject.

21. The device of claim 15, further comprising an initialization unit connected to said analysis unit for establishing initial test conditions and dynamic test parameters,
    said initial test conditions being at least one of test duration, elasticity of said shape, size of said shape, shape of said surface, said target position of said shape, and friction effects between said shape and said surface, and
    said dynamic test parameters being at least one of introduction of changes in the position of said shape at random time intervals, changes in a gravitational constant, and introduction of changes in the position of said shape at user-specified time intervals.

22. The system of claim 15, further comprising an auxiliary test support unit apart from said enclosure and connected to said analysis unit via said communication port.

23. The system of claim 22, wherein said auxiliary test support unit is a computer providing input to, and receiving output from said analysis unit.

24. The system of claim 15, wherein said analysis unit compares current fitness for duty test results to historical fitness for duty test results of the human test subject.

25. The device of claim 21, wherein said initialization unit further establishes a difficulty of the test, and adjusts said test difficulty in response to learning by the human test subject, said test difficulty being determined at least by said desired initial test conditions and said desired dynamic test parameters.

26. The device of claim 15, further comprising a proximity detector located on said exterior surface, said proximity detector detecting contact of the test device with the human test subject at locations other than said two handles.

27. A method for testing a human test subject's fitness for duty, comprising the steps of:
    initializing a hand-held fitness for duty testing device with user-defined test conditions to establish test difficulty, wherein the user-defined test conditions include at least one of a test duration, a contour of a computer-generated surface on a display, target position of a computer-generated shape on the display, elasticity of the shape, size of the shape, roughness of the surface, a simulated gravitational constant, friction effects between the shape and the surface, random changes in position of the shape, and changes in position of the shape at a predetermined time interval;
    positioning the device in the hands of a human test subject;
    displaying the shape on the display, wherein a position of the shape on the display is determined by an orientation of the device;
    providing visual feedback to the human test subject so that the human test subject may attempt to maintain the shape at the target position for a period of time;
    providing test performance data to at least one of a computer, a video display, printer, plotter, memory device, disk drive, and database; and
    providing a test score based on the test performance data.

28. The method of claim 27, further comprising the step of adapting the test difficulty to the human test subject's skill level as learning occurs during conduct of the test.

29. The method of claim 27, further comprising the steps of:
    storing at least one of the test score, the human subject's historical test scores, and the historical test scores of a larger population of test subjects; and
    comparing the test score to historical test scores of the human test subject and to historical test scores of a larger population of test subjects.

30. The method of claim 27, wherein the test performance data comprises an average distance of the shape from the target position.

31. The method of claim 27, wherein the step of determining the test score from the test performance data comprises calculating frequency-domain analysis results, the frequency-domain analysis results comprising at least one of spectral density and cross-spectral density of the test performance data.

* * * * *